US00PP34842P3

(12) United States Plant Patent
de Bont

(10) Patent No.: US PP34,842 P3
(45) Date of Patent: Dec. 13, 2022

(54) ***ECHINACEA* PLANT NAMED 'HILMOOMOTIV'**

(50) Latin Name: *Echinacea purpurea*
Varietal Denomination: Hilmoomotiv

(71) Applicant: TAKII EUROPE B.V., De Kwakel (NL)

(72) Inventor: Diony de Bont, Alphen aan de Rijn (NL)

(73) Assignee: TAKII EUROPE B.V., De Kwakel (NL)

( * ) Notice: Subject to any disclaimer, the term of this patent is extended or adjusted under 35 U.S.C. 154(b) by 0 days.

(21) Appl. No.: 17/562,692

(22) Filed: Dec. 27, 2021

(65) Prior Publication Data

US 2022/0240426 P1 Jul. 28, 2022

Related U.S. Application Data

(60) Provisional application No. 63/140,575, filed on Jan. 22, 2021.

(51) Int. Cl.
*A01H 5/02* (2018.01)
*A01H 6/14* (2018.01)

(52) U.S. Cl.
USPC ..... Plt./428
CPC ..... *A01H 6/1448* (2018.05)

(58) Field of Classification Search
USPC ..... Plt./428
CPC ... A01H 5/02; A01H 5/00; A01H 6/14; A01H 6/1448
See application file for complete search history.

(56) References Cited

PUBLICATIONS

Cpvo Register S2/S3 Publication version 4.1.26, retrieved Feb. 16, 2022, retrieved from the Internet at https://online.plantvarieties.eu/publicConsultationDetails?registerId=20210394&denomination=hilmoomotiv, 3 pp. (Year: 2022).*
Upov Pluto Feb. 23, 2022, retrieved on Feb. 23, 2022, retrieved from the Internet at https://pluto.upov.int/result, one page. (Year: 2022).*

* cited by examiner

*Primary Examiner* — June Hwu
(74) *Attorney, Agent, or Firm* — C. Anne Whealy

(57) ABSTRACT

A new and distinct cultivar of *Echinacea* plant named 'Hilmoomotiv', characterized by its upright to somewhat outward plant habit; moderately vigorous growth habit; freely branching habit, dense and bushy appearance; strong and healthy roots and leaves; dark green-colored leaves; freely flowering habit; strong flowering stems; large inflorescences with light brownish orange-colored ray florets; and good garden performance.

1 Drawing Sheet

Botanical designation: *Echinacea purpurea.*
Cultivar denomination: 'HILMOOMOTIV'.

STATEMENT REGARDING PRIOR DISCLOSURES BY INVENTOR & APPLICANT

A Polish Plant Breeder's Rights application for the instant plant was filed by the Applicant, Takii Europe B.V. of De Kwakel, The Netherlands on Jan. 4, 2021, application number OR 1684. Foreign priority is not claimed to this application.

An European Community Plant Breeder's Rights application for the instant plant was filed by the Applicant, Takii Europe B.V. of De Kwakel, The Netherlands on Feb. 9, 2021, application number 2021/0394. Foreign priority is not claimed to this application.

The Inventor & Applicant assert that no publications nor advertisements relating to sales, offers for sale or public distribution occurred more than one year prior to the effective filing date of this application. Any information about the claimed plant would have been obtained from a direct or indirect disclosure from the Inventor or the Applicant. Inventor & Applicant claim a prior art exception under 35

U.S.C. 102(b)(1) for disclosure and/or sales prior to the filing date but less than one year prior to the effective filing date.

BACKGROUND OF THE INVENTION

The present invention relates to a new and distinct cultivar of *Echinacea* plant, botanically known as *Echinacea purpurea*, and hereinafter referred to by the name 'Hilmoomotiv'.

The new *Echinacea* plant is a product of a planned breeding program conducted by the Inventor in De Kwakel, The Netherlands. The objective of the breeding program is to develop new strong and freely flowering *Echinacea* plants with attractive inflorescences and good garden performance.

The new *Echinacea* plant originated from an open-pollination in April, 2014 in De Kwakel, The Netherlands of a proprietary selection of *Echinacea purpurea* identified as code designation Y, not patented, as the female, or seed, parent with an unknown selection of *Echinacea purpurea* as the male, or pollen, parent. The new *Echinacea* plant was discovered and selected by the Inventor as a single flowering plant from within the progeny of the stated open-pollination grown in a controlled greenhouse environment in De Kwakel, The Netherlands in April, 2015.

Asexual reproduction of the new *Echinacea* plant by in vitro meristem culture in a controlled environment in De Kwakel, The Netherlands since April, 2015 has shown that the unique features of this new *Echinacea* plant are stable and reproduced true to type in successive generations.

SUMMARY OF THE INVENTION

Plants of the new *Echinacea* have been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Hilmoomotiv'. These characteristics in combination distinguish 'Hilmoomotiv' as a new and distinct *Echinacea* plant:

1. Upright to somewhat outward plant habit.
2. Moderately vigorous growth habit.
3. Freely branching habit, dense and bushy appearance.
4. Strong and healthy roots and leaves.
5. Dark green-colored leaves.
6. Freely flowering habit.
7. Strong flowering stems.
8. Large inflorescences with light brownish orange-colored ray florets.
9. Good garden performance.

Plants of the new *Echinacea* can be compared to plants of the female parent selection. Plants of the new *Echinacea* differ from plants of the female parent selection in the following characteristics:

1. Leaves of plants of the new *Echiacea* are darker green in color than leaves of plants of the female parent selection.
2. Plants of the new *Echinacea* are more freely flowering than plants of the female parent selection.
3. Plants of the new *Echinacea* have larger inflorescences than plants of the female parent selection.
4. Ray florets of plants of the new *Echinacea* are light brownish orange in color whereas ray florets of plants of the female parent selection are pink in color.

Plants of the new *Echinacea* can be compared to plants of *Echinacea purpurea* 'Hilmoomedi', not patented. In side-by-side comparisons, plants of the new *Echinacea* differ primarily from plants of 'Hilmoomedi' in the following characteristics:

1. Plants of the new *Echinacea* are not as compact as and have shorter peduncles than plants of 'Hilmoomedi'.
2. Ray florets of plants of the new *Echinacea* are light brownish orange in color whereas ray florets of plants of 'Hilmoomedi' are more orange in color.

BRIEF DESCRIPTION OF THE PHOTOGRAPH

The accompanying photograph illustrates the overall appearance of the new *Echinacea* plant showing the colors as true as it is reasonably possible to obtain in colored reproductions of this type. Colors in the photograph may differ slightly from the color values cited in the detailed botanical description which accurately describe the colors of the new *Echinacea* plant. The photograph is a side perspective view of a typical flowering plant of 'Hilmoomotiv' grown in a container.

DETAILED BOTANICAL DESCRIPTION

The aforementioned photograph and following observations and measurements describe plants grown during the spring and summer in 15-cm containers in a glass-covered greenhouse and "finished" in an outdoor nursery in De Kwakel, The Netherlands under cultural practices typically used in commercial *Echinacea* production. During the production of the plants, greenhouse day temperatures ranged from 12° C. to 14° C., outdoor nursery day temperatures ranged from 14° C. to 20°, greenhouse night temperatures ranged from 12° to 14° and outdoor nursery night temperatures ranged from 7° C. to 15° C. Plants were 25 weeks from planting when the photograph and description were taken. In the following description, color references are made to The Royal Horticultural Society Colour Chart, 2015 Edition, except where general terms of ordinary dictionary significance are used.

Botanical classification: *Echinacea purpurea* 'Hilmoomotiv'.

Parentage:

*Female parent.*—Proprietary selection of *Echinacea purpurea* identified as code designation Y, not patented.

*Male parent.*—Unknown selection of *Echinacea purpurea*, not patented.

Propagation:

*Type.*—By in vitro meristem culture.

*Time to initiate roots, summer.*—About five weeks at temperatures about 20° C. for the first two weeks, then at temperatures about 12° C. to 14° C.

*Time to initiate roots, winter.*—About six weeks at temperatures about 20° C. for the first two weeks, then at temperatures about 14° C. to 20° C.

*Time to produce a rooted young plant, summer.*—About five weeks at temperatures about 14° C. to 20° C.

*Time to produce a rooted young plant, winter.*—About six weeks at temperatures about 18° C.

*Root description.*—Medium in thickness, fibrous; strong and healthy; typically white to brown in color, actual color of the roots is dependent on substrate composition, water quality, fertilizer type and formulation, substrate temperature and physiological age of roots.

*Rooting habit.*—Moderately freely branching; medium density.

Plant description:

*Plant form and growth habit.*—Herbaceous perennial; upright to somewhat outward plant habit, broadly ovate to oblong in overall shape; freely branching habit with about twelve branches developing per plant; moderately vigorous growth habit and slow to moderate growth rate.

*Plant height.*—About 37 cm.

*Plant diameter or spread.*—About 32.9 cm.

*Lateral branches.*—Length: About 14 cm. Diameter: About 4.5 mm. Internode length: About 1.8 cm. Aspect: Erect to about 10° from vertical. Strength: Strong. Texture: Moderately pubescent, strigose; rough. Color: Close to 144A.

Leaf description:

*Basal and cauline leaves.*—Arrangement: Alternate, simple. Length: About 10.6 cm. Width: About 3.8 cm. Shape: Narrowly ovate. Apex: Acute to narrowly acute. Base: Attenuate. Margin: Entire; moderately undulate. Texture and luster, upper and lower surfaces: Sparsely to moderately pubescent, strigose; rough; not rugose; slightly glossy. Venation pattern: Pinnate. Color: Developing leaves, upper surface: Close to a blend of 143A and 146B. Developing leaves, lower surface: Close to 146B. Fully expanded leaves, upper surface: Close to NN137A; venation, close to 145A. Fully expanded leaves, lower surface: Close to 147B; venation, close to 146D. Petioles: Basal leaves, length: About 4.2 cm. Cauline leaves, length: About 2 mm. Diameter, basal and cauline leaves: About 2.25 mm. Strength: Strong, flexible. Texture, upper and lower surfaces: Sparsely pubescent; strigose. Color, upper surface: Close to NN137A; midvein, close to 146D; proximally, basal leaves, slightly tinged with close to 176B. Color, lower surface: Close to 138A; midvein, close to 146D.

Inflorescence description:

*Appearance.*—Terminal rotate single-type inflorescences with ray and disc florets arranged on a capitulum; inflorescences positioned upright above the foliar plane on mostly upright and strong peduncles.

*Flowering habit.*—Freely flowering habit with more than 24 open inflorescences per plant at one time.

*Fragrance.*—None detected.

*Time to flower.*—Plants begin flowering about four weeks after flower bud development; in the garden, plants flower continuously from early May to mid-November in The Netherlands.

*Inflorescence longevity.*—Inflorescences maintain good substance for about three weeks on the plant; inflorescences persistent.

*Inflorescence buds.*—Height: About 2.5 cm. Diameter: About 3 cm. Shape: Flattened globular. Color: Involucral bracts, slightly darker and more intense than 146B tinged with close to 172A; immature ray florets, close to N170C and at the apices, close to 150A to 150B.

*Inflorescence size.*—Diameter: About 8.2 cm. Depth (height): About 4.2 cm. Disc diameter: About 2.8 cm.

*Receptacles.*—Height: About 7 mm. Diameter: About 8 mm. Shape: Broadly ovate. Color: Close to 155B.

*Ray florets.*—Quantity and arrangement: About 17 to 24 arranged in about two whorls at the base of the receptacle. Length: About 3.7 cm. Width: About 1.15 cm. Shape: Oblanceolate. Apex: Praemorse. Base: Cuneate. Margin: Entire. Texture and luster, upper surface: Smooth, glabrous; velvety; moderately carinate; matte. Texture and luster, lower surface: Sparsely pubescent; slightly glossy. Aspect: Horizontal to drooping, eventually about 40° from horizontal. Color: When opening, upper surface: Close to 38A; distally, tinged with close to 37A and 37B. When opening, lower surface: Close to 54B and 54C and at the apex, close to N144D. Fully opened, upper surface: Close to 51B; distally, tinged with close to 43D; venation, similar to lamina color; color becoming closer to slightly lighter than 59D and at the apex, close to 146D, with subsequent development. Fully opened, lower surface: Close to N170D slightly tinged with close to 75D and towards the apex, close to 59D; venation, similar to lamina color; color becoming closer to 174C and 174D and towards the apex, close to 146B and venation, close to 197C and 197D, with subsequent development.

*Disc florets.*—Quantity and arrangement: About 300 spirally arranged at the center of the inflorescence. Length: About 1 cm. Diameter: About 3 mm. Shape: Lower 87.5% fused into a tube, apices acute; free margins, entire. Texture and luster, inner and outer surfaces: Smooth, glabrous; moderately glossy. Color, immature, inner and outer surfaces: Distally, close to N148A and slightly tinged with close to 182B and 182C at the apex; proximally, close to 146D. Color, mature, inner and outer surfaces: Distally, close to N148B and proximally, close to 151B.

*Receptacle spines.*—Quantity: One per disc floret. Shape: Acicular. Apex: Acute. Base: Attenuate. Texture and luster: Smooth, glabrous; glossy. Color: Apex: Close to 24A and at the apex, close to N45A to N45B. Mid-section: Close to 147C. Base: Close to 145C to 145D.

*Involucral bracts.*—Quantity and arrangement: About 68 arranged in about three whorls. Length: About 1 cm. Width: About 3 mm. Shape: Oblong to narrowly ovate; apex, reflexed. Apex: Acute. Base: Cuneate. Margin: Entire. Texture and luster, upper surface: Smooth, glabrous; slightly glossy. Texture and luster, lower surface: Smooth and mostly glabrous, margins are moderately pubescent; matte. Color, upper surface: Close to NN137A and towards the base, close to 137B. Color, lower surface: Close to NN137B.

*Peduncles.*—Length: About 12.1 cm. Diameter: About 4 mm. Strength: Strong. Aspect: Upright. Texture: Moderately pubescent, strigose. Color: Close to 144A slightly blotched with close to 146B.

*Reproductive organs.*—Androecium (present on ray and disc florets): Quantity per floret: About five. Filament length: About 4 mm. Filament color: Close to 157A. Anther shape: Narrowly oblong. Anther length: About 3.5 mm. Anther color: Close to 200A. Pollen amount: Scarce to moderate. Pollen color: Close to 23A. Gynoecium (present only on disc florets): Quantity per floret: One. Pistil length: About 6 mm. Stigma shape: Decurrent, unequal. Stigma color: Close to 34B. Style length: About 5 mm. Style color: Close to 150D. Ovary color: Close to 157A. Seeds and fruits: To date, seed and fruit development have not been observed on plants of the new *Echinacea*.

Pathogen & pest resistance: To date, plants of the new *Echinacea* have not been shown to be resistant to pathogens and pests common to *Echinacea* plants.

Garden performance: Plants of the new *Echinacea* have exhibited good garden performance and to tolerate rain and wind. Plants of the new *Echinacea* have been observed to tolerate high temperatures of about 35° C. and to be hardy to USDA Hardiness Zones 3 to 4.

It is claimed:

1. A new and distinct *Echinacea* plant named 'Hilmoomotiv' as illustrated and described.

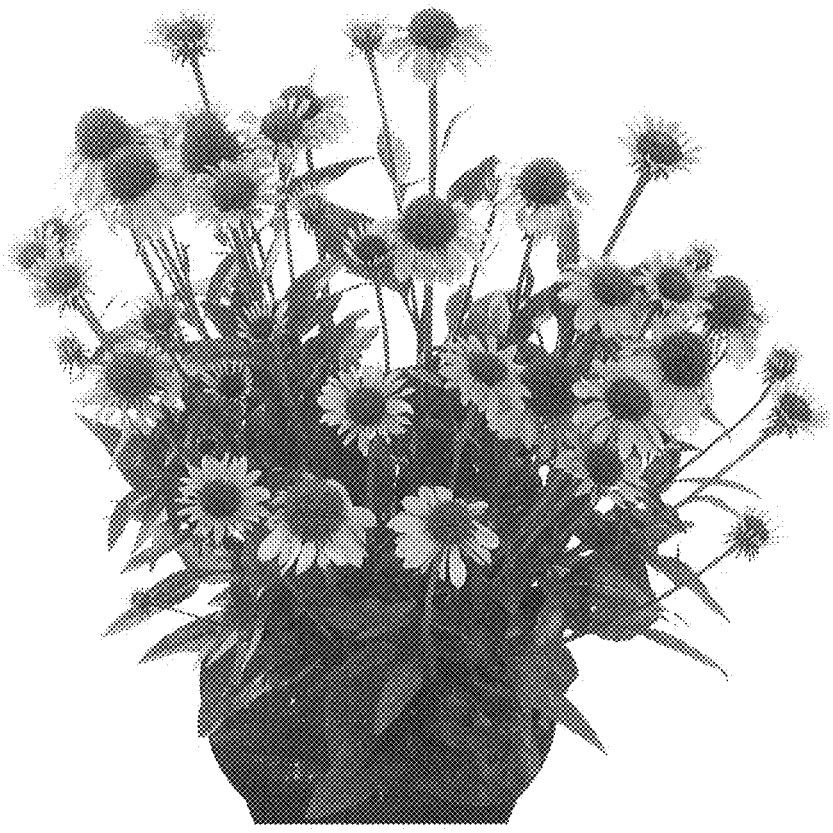

* * * * *